(12) United States Patent
Bender (10) Patent No.: US 8,906,115 B2
(45) Date of Patent: Dec. 9, 2014

(54) METHOD FOR THE ANTIMICROBIAL FINISHING OF TEXTILES AND FIBERS

(75) Inventor: Walter Bender, Rheinfelden (CH)

(73) Assignee: Sanitized AG (CH)

(*) Notice: Subject to any disclaimer, the term of this patent is extended or adjusted under 35 U.S.C. 154(b) by 0 days.

(21) Appl. No.: 12/518,477

(22) PCT Filed: Dec. 11, 2007

(86) PCT No.: PCT/EP2007/063663
§ 371 (c)(1),
(2), (4) Date: Dec. 17, 2009

(87) PCT Pub. No.: WO2008/071680
PCT Pub. Date: Jun. 19, 2008

(65) Prior Publication Data
US 2010/0115706 A1   May 13, 2010

(30) Foreign Application Priority Data
Dec. 12, 2006 (DE) .......................... 10 2006 058 790

(51) Int. Cl.
| | | |
|---|---|---|
| *C11D 3/00* | (2006.01) | |
| *D06M 15/423* | (2006.01) | |
| *D06P 1/673* | (2006.01) | |
| *D06P 5/00* | (2006.01) | |
| *D06M 15/643* | (2006.01) | |
| *D06M 13/46* | (2006.01) | |
| *D06M 11/45* | (2006.01) | |
| *D06M 11/46* | (2006.01) | |
| *D06M 11/71* | (2006.01) | |
| *D06M 16/00* | (2006.01) | |
| *D06M 11/20* | (2006.01) | |
| *A01N 55/00* | (2006.01) | |
| *A01N 33/12* | (2006.01) | |
| *D06M 11/17* | (2006.01) | |
| *D06M 13/513* | (2006.01) | |
| *D06M 11/56* | (2006.01) | |
| *C08K 5/544* | (2006.01) | |

(52) U.S. Cl.
CPC .............. *D06M 13/46* (2013.01); *D06M 11/45* (2013.01); *D06M 11/46* (2013.01); *D06M 11/71* (2013.01); *D06M 16/00* (2013.01); *D06M 11/20* (2013.01); *A01N 55/00* (2013.01); *A01N 33/12* (2013.01); *D06M 11/17* (2013.01); *C08K 5/544* (2013.01); *D06M 13/513* (2013.01); *D06M 11/56* (2013.01)

USPC ............. 8/115.51; 8/115.6; 8/115.65; 8/490; 252/8.61

(58) Field of Classification Search
USPC ......... 8/115.51, 115.6, 115.65, 490; 252/8.61
See application file for complete search history.

(56) References Cited

U.S. PATENT DOCUMENTS

| | | | |
|---|---|---|---|
| 3,788,803 A | 1/1974 | Klein et al. | |
| 4,576,728 A * | 3/1986 | Stoddart | 510/373 |
| 4,615,882 A | 10/1986 | Stockel | |
| 5,411,585 A * | 5/1995 | Avery et al. | 106/287.1 |
| 6,228,127 B1 * | 5/2001 | Reinehr et al. | 8/111 |
| 6,376,696 B1 | 4/2002 | Raab et al. | |
| 6,387,856 B1 * | 5/2002 | Ofosu-Asante et al. | 510/131 |
| 6,673,761 B2 * | 1/2004 | Mitra et al. | 510/384 |
| 6,740,626 B2 * | 5/2004 | Neumiller | 510/109 |
| 2004/0261196 A1 * | 12/2004 | Ghosh et al. | 8/147 |
| 2005/0182140 A1 * | 8/2005 | Payne | 514/643 |
| 2007/0065475 A1 * | 3/2007 | Elfersy | 424/405 |
| 2011/0065346 A1 | 3/2011 | Bender et al. | |

FOREIGN PATENT DOCUMENTS

| | | |
|---|---|---|
| DE | 199 28 127 C1 | 5/2000 |
| WO | 00/78770 A1 | 12/2000 |
| WO | 2004/087226 A1 | 10/2004 |
| WO | 2005/069785 A2 | 8/2005 |
| WO | 2005/069785 A3 | 8/2005 |
| WO | 2007/135163 A1 | 11/2007 |

OTHER PUBLICATIONS

International Search Report Issued in the Corresponding International Application PCT/EP2007/063663, Completed on Apr. 17, 2008 and Mailed on Apr. 25, 2008.

International Search Report issued in the Corresponding International Application No. PCT/EP2007/063665, Completed on Mar. 31, 2008, and Mailed on Apr. 8, 2008.

Jun. 7, 2013, Office Action in U.S. Appl. No. 12/518,216.

* cited by examiner

*Primary Examiner* — Harold Pyon
*Assistant Examiner* — Tanisha Diggs
(74) *Attorney, Agent, or Firm* — J.A. Lindeman & Co., PLLC (57) ABSTRACT

A method for the antimicrobial finishing of synthetic fibers, in which an aqueous solution of an organic primer component (P), such as, for example, gallic acid, and, as antimicrobial component (K), at least one organic quaternary ammonium compound, and a metal salt component (M) are applied at the same time or at a different time to the fibers, permits permanent antimicrobial finishing.

6 Claims, 1 Drawing Sheet

METHOD FOR THE ANTIMICROBIAL FINISHING OF TEXTILES AND FIBERS

This is a National Phase Application in the United States of International Patent Application No. PCT/EP2007/063663 filed Dec. 11, 2007, which claims priority on European Patent Application No. 10 2006 058 790.1 filed Dec. 12, 2006.

The present invention relates to a method for the permanent antimicrobial finishing of textiles and fibers. In this, firstly an organic primer component (P) and secondly an organic antimicrobial component (K) are applied to the textiles and fibers. The composition used for this purpose or the compositions used can comprise, besides one or more solvents, if appropriate also a metal salt component (M) and further auxiliary components.

The prior art already describes various methods for the finishing of textiles and fibers with antimicrobial components which, for example, increase the wear comfort of items of clothing. Most textiles contain microbiodegradable material. They are often manufactured either entirely or in part from microdegradable fibers, for example from cotton, cellulose (e.g. viscose and tencel), hemp, flax, linen, silk, acetate or wool. Textiles made of synthetic components such as, for example, polyester, polyacrylonitrile, polyamide (e.g. Aramid, Nomex, Kevlar, Polyamid 6, Polyamid 6.6) or polypropylene, are also regularly inhabited by bacteria, particularly when they are provided with finishing agents, such as, for example, plasticizers, hydrophobicizing agents, antistats; fluorocarbons and/or binders, or absorb microbiodegradable material during use, such as, for example, organic substances from the environment.

The infestation of the textiles with microorganisms such as bacteria can adversely modify not only the optical properties but also the use properties of the textiles.

The organic constituents of apocrine perspiration, a liquid which is virtually odorless upon emerging from the glands, are decomposed within a short time by bacteria of the skin flora. This also occurs on textile materials which come into contact with perspiration. The small molecules which are formed from the degradation of e.g. long-chain fatty acids or hormones, such as, for example, testosterone, such as butyric acid or formic acid, lead to an undesired perspiration odor.

In this connection, textiles made of synthetic fibers, such as, for example, polyester or polyamide, are particularly susceptible to bacterial degradation of perspiration and can consequently have the typical unpleasant odor of decomposed perspiration after a particularly short time.

As is known, the occupation by microorganisms and the degradation of perspiration can be prevented by an antimicrobial finishing of textiles. For the antibacterial finishing of textiles, in the prior art, e.g. substances such as triclosan (a phenoxyphenol derivative) or more recently also preparations based on silver ions are used. From a technical perspective, however, products containing these substances have their narrow limits. For example, the vapor pressure of triclosan on the tenter and the achievable resistance to washing in the case of the silver products available hitherto, especially when no polymeric binder is applied, are disadvantageous. The avoidance of binders, however, is often necessary since polymeric binders alter the feel of textiles which, as an effect, is not always desired. U.S. Pat. No. 3,788,803 discloses a treatment of synthetic fibers with halophenols in combination with phthalic acid esters.

There has hitherto been no satisfactory method for the antibacterial finishing of textiles and fibers which contain synthetic components and/or consist of these.

The object of a permanent antimicrobial and/or antibacterial finishing, in particular on textiles which consist completely or partially of synthetic fibers such as polyamide or polyester, has hitherto been inadequately achieved. Particularly in the case of sensitive textiles, on the other hand, the need for antimicrobial finishing is very great since such textiles are often used for applications in the sport and leisure sector, where the textile properties of these fibers are very particularly desired, but on the other hand the contamination of the textile by perspiration is very great precisely during sorting activities.

Food, heat and moisture, the fundamentals of bacterial growth, moreover, arise especially in the case of sports textiles.

Besides clothing textiles, there are increasingly applications of synthetic fibers such as polyamide and in particular polyester in the field of household textiles, where such fibers are often used as microfibers. Examples of such applications of synthetic fibers are microfiber wipes for cleaning, terry toweling, or as cushion cover materials.

Besides the antibacterially effective substances already mentioned above, the use of quaternary ammonium compounds (so-called "quats") for the antibacterial finishing of textiles is described in the literature. Substances of this class often cover a broad germ spectrum with an excellent effect. For example, Karl Heinz Wallhäusser, Praxis der Sterilisation Desinfektion—Konservierung [Practice of sterilization disinfection—preservation], 5th edition, Georg Thieme Verlag Stuttgart, New York 1995, page 586 ff. describes this substance class in detail. It has been known for a long time that quaternary ammonium compounds have a bactericidal action when at least one of the four substituents on the quaternary nitrogen has a chain length of from 8 to 18 carbon atoms, preferably one of 12 to 16 carbon atoms.

The other substituents can be, for example, straight or branched alkyl radicals or radicals with heteroatoms or radicals with aromatics. One or more benzyl radicals are also often bonded to the quaternary nitrogen in the molecule. Good results were also found with quaternary ammonium compounds with two methyl groups, one n-alkyl group having between 10 and 18 carbon atoms and a 3-trimethoxysilylpropyl group.

Quaternary ammonium compounds have the positive property that they are readily soluble in water. This property fits in very well with aqueous application in the industrial finishing process in the textile industry. However, at the same time this property leads to such compounds being rapidly washed out of the textiles since the adhesion to textiles is possible primarily by means of Van-der-Waals forces and if appropriate also with ion-pair bonds.

In order to improve the resistance to washing of textiles, the precursors of the quats, namely tertiary amines, have been quaternized with 3-chloropropyltrimethoxysilane. If this quaternization is carried out in the solvent methanol, then this reaction has already been known for decades.

On the market there are, for example, products with a trimethoxysilylpropyl group on the quaternary nitrogen, where the products can be obtained from the reaction with didecylmethylamine or with tetradecyldimethylamine or from the reaction with octadecyldimethylamine. The solvent-free quaternization of amines is described, for example, in DE-A 199 28 127.

The quaternization can also take place with the octadecyldimethylamine in methanol, but then leads to a product which is not optimal with regard to the antibacterial effect. The main disadvantage of this product is the solvent methanol which, on account of its properties, leads to considerable application limitations in the textile industry.

Textiles made of polyester have hitherto already been finished with a formulation with the active ingredient dimethyltetradecyl[3-(trimethoxysilyl)propyl]ammonium chloride, which is on the market as Sanitized T 99-19 (manufacturer: Sanitized AG, Switzerland). Here, a 50% strength solution of the technical-grade active ingredient (salt) in methyl triglycol is present. Methyl triglycol has the chemical formula $CH_3(OCH_2CH_2)_3$—OH.

The likewise known product Aegis AEM 5772/5 (manufacturer: Aegis) is an approximately 5% strength aqueous solution of the active ingredient dimethyloctadecyl[3-(trimethoxysilyl)propyl]ammonium chloride. Alternatively, the more highly concentrated active ingredient dissolved in methyl alcohol is also available.

During the preparation of the application baths, the hydrolysis products of the active ingredients are very rapidly formed, which have a tendency toward oligomerization, if they are not already present in the commercial form as predominantly hydrolyzed product.

The finishings of the textiles have hitherto preferably taken place in the padding process. If these textiles are tested using a count test in accordance with the method JIS L 1902:2002 or according to the standard ASTM E 21-49, then they exhibit an excellent antibacterial effect.

On textiles made of cellulose fibers, these known products find reaction partners with which they can react chemically and enter into a stable covalent bond. The antimicrobial finishing is permanent on such textiles.

By contrast, on polyester or polyamide there are few reaction partners in order to bond such products permanently. If these textiles are washed, then the antibacterial effect in most cases disappears largely to completely after just a few wash cycles.

It is therefore an object to find a technical solution as to how organic quaternary ammonium compounds, in particular those with a trimethoxysilylalkyl group as radical on the quaternary ammonium group (or the hydrolysis forms thereof) can be applied to textiles which have been manufactured largely or completely by synthetic fibers, such as, for example, polyamide or polyester, in as wash-resistant a manner as possible. There is a need for methods which permit permanent antimicrobial finishing and can be applied easily and cost-effectively. In particular polyamide and polyester are of interest as target substrate for wash-resistant finishings. Here, wash-resistant is used to describe a detectable antibacterial effect after at least 20 wash cycles in accordance with the standard EN ISO 6330 (6A) at 40° C.

The detection takes place e.g. in a test in accordance with the standards JIS L 1902:2002 or ASTM E 21-49 against *Staphylococcus aureus* (ATCC 6538). The germ count reduction between finished and nonfinished samples or between finished sample following incubation and the germ count of the inoculum should be approximately two factors of ten in order to be able to speak of a good antibacterial effect.

The aforementioned objects are achieved by a method for the antimicrobial finishing of textiles and/or fibers which contain at least one synthetic component (e.g. polyamide or polyester) (or consist of these), in which a preferably aqueous solution of an organic primer component (P), which increases the hydrophobicity of the surface of the textiles or fibers, and, as antimicrobial component (K), at least one organic quaternary ammonium compound are applied to the textiles or fibers. In addition, if appropriate a metal salt component (M) and if appropriate a solvent (L) and if appropriate further auxiliary components can also be applied to the textiles or fibers at the same time or at a different time.

The method as claimed in the invention can be carried out in numerous variants, a "two-bath process" having proven useful. However, it is also possible to carry out a so-called "one-bath process" or to realize multistage baths. In one particular embodiment of the invention, a method is carried out in which an aqueous solution of an organic primer component (P) is used which additionally comprises, as antimicrobial component (K), at least one organic quaternary ammonium compound, and if appropriate a metal salt component (M). In this variant, e.g. in an aqueous composition, the organic primer component (P) and the quaternary ammonium compound are already combined, meaning that a simplified finishing according to the "one-bath method" is possible.

In a further embodiment of the invention, a method is carried out in which a plurality of process steps are carried out in succession. Thus, firstly a process step a) of the pretreatment of the textiles or fibers with an aqueous solution of an organic primer component (P) can take place. Then, if appropriate, a thermal drying step b) is carried out, and subsequently, in a further process step c), a treatment of the textiles or fibers with a, for example, aqueous solution comprising as antimicrobial component (K) at least one organic quaternary ammonium compound, and if appropriate a metal salt component (M) and if appropriate one or more solvents (L) and if appropriate further auxiliary components is carried out.

In The method as claimed in the invention, preference is given to using an aqueous solution of an organic primer component (P). Suitable primer components are a large number of organic molecules which are able to increase the hydrophobicity of the surface of the textiles or fibers.

This requires that the molecule can interact with the synthetic fibers via an as a rule hydrophobic molecular moiety and, secondly, can react with the antimicrobial component via a hydrophilic molecular moiety.

During the treatment of the textile with the primer component, heating of the aqueous solution comprising the textile and the primer component (e.g. to a temperature from 40 to 90° C.) is often carried out. The treatment can also be carried out in a high-temperature extractive method (e.g. at temperatures of from 100 to 140° C., in particular at about 120° C.).

Preferably, the primer component (P) consists e.g. of one or more of the following compounds:
  aromatic mono- and dicarboxylic acids, where these may also be substituted by hydroxy groups;
  aromatic mono- and diamines, aromatic mono- or dialcohols;
  aliphatic mono- and dicarboxylic acid having 6 to 26 carbon atoms, where these may also be substituted by hydroxy or amino groups;
  aliphatic, primary, secondary and tertiary amines having 6 to 26 carbon atoms;
  aliphatic, primary and secondary alcohols having 6 to 26 carbon atoms;
  aliphatic, primary mercaptans having 6 to 26 carbon atoms;
  natural and nonnaturally occurring amino acids, for example the amino acid phenylalanine.

Organosilicon compounds with at least one long-chain alkyl group and relatively high molecular weight condensation products with free hydroxy and/or carboxyl groups (such as the natural product rosin) or else oligomeric esters can also in principle be used as primer component (K).

In a further embodiment of the invention, a method is carried out in which the textiles or fibers treated with an aqueous solution are subjected to at least one drying step, where a temperature of at least 100° C., preferably of 100 to 180° C., is used. The drying step can take place, for example, after the treatment of the textiles or fibers with the solution comprising the primer component (P). The temperature used here is dependent on the material of the textiles and fibers since the different materials have different glass transition temperatures. The glass transition temperature of a pure polyester material can be e.g. 98° C., that of a mixed polymer material e.g. at 74° C. In the literature, glass transition temperatures of about 70° C. to just above 100° C. are described in general.

If a temperature of at least 100° C., preferably of 100 to 180° C., in particular 110 to 160° C., is used in the drying step, this temperature is generally above the glass transition temperature of the treated material. By virtue of this step, the primer component can be dissolved at least partially in the material of the textiles or fibers.

Depending on the method used, the thermal treatment generally lasts from 1 second up to 10 minutes, preferably from 2 seconds to 4 minutes, in particular from 3 seconds to 2 minutes.

In a further embodiment of the invention, a method is carried out in which an antimicrobial component (K) and if appropriate a metal salt component (M) and also if appropriate a solvent (L) and if appropriate further auxiliary components are used, where component (K) is a compound of the general formula (I)

where the radicals, independently of one another, have the following meanings,
- $R^1$ is a branched or unbranched alkyl radical having 1 to 12 carbon atoms, where the alkyl radical may also be substituted by a group $H-((CH_2)_m-O)_q$, where m may be an integer from 0 to 4 and q is an integer from 1 to 6;
- $R^2$ is a branched or unbranched alkyl radical having 1 to 12 carbon atoms, where the alkyl radical may also be substituted by a group $H-((CH_2)_m-O)_q$, where m may be an integer from 0 to 4 and q is an integer from 1 to 6;
- $R^3$ is a branched or unbranched alkyl radical having 1 to 12 carbon atoms, where the alkyl radical may also be substituted by a group $H-((CH_2)_m-O)_q$, where m may be an integer from 0 to 4 and q is an integer from 1 to 6;
- $R^4$ is a branched or unbranched alkyl radical having 1 to 18 carbon atoms, a cycloalkyl radical having 3 to 7 carbon atoms, a phenyl radical, a benzyl radical optionally substituted by one or two halogen atoms or a heteroaryl radical;
- $R^5$ is a branched or unbranched alkyl radical having 1 to 18 carbon atoms, a cycloalkyl radical having 3 to 7 carbon atoms, a phenyl radical, a benzyl radical optionally substituted by one or two halogen atoms or a heteroaryl radical;
- $R^6$ is a branched or unbranched alkyl radical having 8 to 18 carbon atoms;
- n is an integer from 1 to 6.

The metal salt component (M), so far as it is likewise used, preferably comprises here at least one salt of a di- to pentavalent metal.

An alkyl radical is to be understood as meaning, e.g. a methyl, ethyl, propyl, butyl, hexyl, heptyl or octyl radical, but also e.g. the long-chain radicals such as octyl, decyl, dodecyl, tetradecyl, hexadecyl or the octadecyl radical. In this connection, these radicals may also be branched, or unbranched, chiral or achiral.

The term cycloalkyl is understood as meaning mono- or bicyclic saturated groups having 3 to 8 carbon atoms, e.g. cyclohexyl, cyclopentyl or cyclopropyl, with cyclohexyl being preferred.

The term "benzyl radical optionally substituted by one or two halogen atoms" is understood as meaning various mono- or disubstituted benzyl radicals which are substituted e.g. by fluorine, chlorine or bromine.

The term heteroaryl is understood as meaning mono- or bicyclic unsaturated radicals which comprise one or more "heteroatoms" (e.g. N, O, or S). These radicals can comprise e.g. 6-membered and/or 5-membered rings. Examples of nitrogen-containing radicals which may be mentioned are: pyridine, pyrimidine, pyrazine, pyridazine, pyrrole, imidazole, triazole; examples of sulfur-containing radicals are: thiophene or thiazole; and examples of oxygen-containing radicals are: furan or oxazole.

On account of the quaternary structure on the nitrogen atom, there is a positive charge in the molecule, which can be compensated e.g. by counterions. Typical anions in the salts are e.g. chloride, bromide, fluorides, sulfate, phosphates, formates, acetates or propionates. Preference is given to using chlorides.

Preference is given to using a method in which an antimicrobial component (K) of the general formula (I) is used, where the radicals, independently of one another, have the following meanings:
- $R^1$ is an alkyl radical having 1 to 6 carbon atoms, where the alkyl radical may also be substituted by a group $H-((CH_2)_m-O)_q$, where m may be an integer from 1 to 3 and q is an integer from 1 to 4;
- $R^2$ is an alkyl radical having 1 to 6 carbon atoms, where the alkyl radical may also be substituted by a group $H-((CH_2)_m-O)_q$, where m may be an integer from 1 to 3 and q is an integer from 1 to 4;
- $R^3$ is an alkyl radical having 1 to 6 carbon atoms, where the alkyl radical may also be substituted by a group $H-((CH_2)_m-O)_q$, where m may be an integer from 1 to 3 and q is an integer from 1 to 4;
- $R^4$ is an alkyl radical having 1 to 18 carbon atoms, a cycloalkyl radical having 3 to 7 carbon atoms, a phenyl radical, a benzyl radical optionally substituted by one or two halogen atoms, a pyridine radical, a pyrimidine radical, a pyrazine radical, a pyridazine radical, a pyrrole radical or an imidazole radical;
- $R^5$ is an alkyl radical having 1 to 18 carbon atoms, a cycloalkyl radical having 3 to 7 carbon atoms, a phenyl radical, a benzyl radical, a pyridine radical, a pyrimidine radical, a pyrazine radical, a pyridazine radical, a pyrrole radical or an imidazole radical;
- $R^6$ is an alkyl radical having 8 to 18 carbon atoms;
- and n is an integer from 1 to 4.

Preference is also given to using a method in which an antimicrobial component (K) of the general formula (I) is used, where the radicals, independently of one another, have the following meanings:
- $R^1$, $R^2$, $R^3$ are in each case an alkyl radical having 1 to 6 carbon atoms, where the alkyl radical may also be substituted by a group $H-((CH_2)_m-O)_q$, where m may be an integer from 1 to 3 and q is an integer from 1 to 4;
- $R^4$ is an alkyl radical having 1 to 18 carbon atoms, a phenyl radical or a benzyl radical,
- $R^5$ is an alkyl radical having 1 to 18 carbon atoms;

$R^6$ is an alkyl radical having 8 to 18 carbon atoms; and n is an integer from 2 to 4.

Particular preference is given to using a method in which an antimicrobial component (K) of the general formula (I) is used, where the radicals, independently of one another, have the following meanings:

$R^1$, $R^2$ and $R^3$ are identical and are a branched or unbranched alkyl radical having 1 to 4 carbon atoms, n is an integer from 1 to 4

$R^4$ is methyl, $R^5$ is alkyl having 1 to 12 carbon atoms, and $R^6$ is alkyl having 8 to 18 carbon atoms.

Preference is also given to using a method in which an antimicrobial component (K) and additionally a metal salt component (M) are used, where this metal salt component (M) comprises at least one salt of a divalent, trivalent or tetravalent metal. In a particular embodiment, the metal salt component (M) consists of one or two salts of a divalent, trivalent and/or tetravalent metal. The metal salt component (M) used is preferably at least one salt of a divalent, trivalent or tetravalent metal from the group of the following metals: Mg, Ca, Ba, Zn, Sn; Al, Ga, Fe; and Ti.

As metal salt component (M), preference is given to using a metal salt component (M) which comprises at least one salt of a divalent metal from the group Mg, Ca, Ba, Zn and/or a salt of a trivalent metal from the group Al and Fe, where the combination of Ca with Al or Fe is attributed particular importance. In particular, the combination of aluminum III salts with divalent metal salts has proven useful.

In one preferred embodiment, the invention relates to a composition which comprises, as organic component (K) of the general formula (I), a dimethyltetradecyl(3-(trimethoxysilyl)propyl)ammonium salt, e.g. a chloride, or a dimethyloctadecyl(3-(trimethoxysilyl)propyl)ammonium salt, e.g. a chloride, and, as metal salt component (M), comprises a salt of a divalent metal from the group Mg, Ca, Zn and/or a salt of a trivalent metal from the group Al and Fe.

In this connection, suitable counterions in the metal salts are various anions, e.g. the chlorides, hydroxides, sulfates, phosphates and acetates.

The antimicrobial compositions according to the invention comprise the two components (organic component (K) and metal salt component (M)) preferably in specific amounts. In this connection, within the context of the present invention, data in % by weight is used.

Textile pretreatment or aftertreatment compositions may be in solid, liquid or flowable form, e.g. as gel, powder, granules, paste or spray, and comprise the aforementioned components according to the invention.

The compositions comprise the metal salt component (M) preferably in amounts of from 0.01 to 20% by weight, preferably 0.01 to 10% by weight, more preferably from 0.05 to 2.0% by weight and in particular from 0.02 to 2.0% by weight, based on the total composition.

The organic component (K) is preferably used, based on the total weight of the composition, in an amount of from 0.01% by weight to 10% by weight, preferably 0.1% by weight to 3.0% by weight, and in particular from 0.3% by weight to 2.5% by weight.

The ratio between metal component (M) and organic component (K) is dependent on the metal salt used and, in the antimicrobial composition, is e.g. from 1:20 to 20:1, in particular from 1:10 to 10:1, based on the molar amounts used. If e.g. a trivalent metal salt is used, then the ratio of the components is often from 2:1 to 1:2, in particular about 1:1. Moreover, preference is given to using mixtures of di- and trivalent metal salts.

A further embodiment relates to a method in which an antimicrobial component (K) is used which comprises a dimethyltetradecyl(3-(trimethoxysilyl)propyl)ammonium salt or a dimethyloctadecyl(3-(trimethoxysilyl)propyl)ammonium salt, and where additionally if appropriate a metal salt component (M) is used which comprises a salt of a divalent metal from the group Mg, Ca, Zn, Ba and/or a salt of a trivalent metal from the group Al and Fe.

For both process steps a) and c), the solvent used is preferably water. If appropriate, an alcohol, e.g. ethanol, methanol, isopropanol or propanol, can additionally be used. The preparations can also comprise various auxiliary components, e.g. a pH buffer (such as acetic acid/sodium acetate) or an acid (such as formic acid, citric acid or acetic acid).

In a further embodiment of the invention, the composition further comprises, for example, one or more of the following auxiliaries:

pH buffers, softeners, fluorocarbons, hydrophobicizing agents, oleophobicizing agents, binders, crosslinkers, flame retardants, textile dyes, sewability improvers and soil release agents.

One preferred embodiment relates to a method in which an aqueous solution of an organic primer component (P) is used, where this solution comprises from 0.001 to 25% by weight, in practice also 0.01 to 15% by weight, in particular 0.02 to 10% by weight, and preferably from 0.1 to 3% by weight, of the primer component (P). Instead of a primer compound, two, three or more primers can also be used together or at different times.

The quantitative data for the components in the liquor is industrially only useful to a limited extent since the liquor ratio is not a pregiven parameter and in practice is from ca. 1:4 (mass of textile:mass of liquor) up to 1:20 and in extreme cases is even considerably higher still. The preferred concentration range for the primer P, for example L-phenylalanine, based on the textile mass, is in the range 1 to 3%, e.g. ca. 2%. If, for example, a liquor ratio of 1:5 is used, then this means that between 0.2 and 0.6% by weight of L-phenylalanine are in the liquor. If a somewhat differently constructed apparatus is used but which produces the same result, namely 1 to 3% of L-phenylalanine on the textile in a similar extractive process, but the liquor is used in the ratio 1:20, then L-phenylalanine is in the liquor in a concentration range from 0.05 to 0.15%.

A further embodiment relates to a method in which an aqueous solution of an antimicrobial component (K) is used, this solution comprising from 0.01 to 10% by weight, preferably 0.1 to 10% by weight, in some cases also from 0.1 to 3% by weight, of the antimicrobial component (K). This solution can also additionally comprise from 0.01 to 10% by weight, in particular from 0.05 to 2% by weight, of a metal salt component (M).

Often, an amount of from 0.3 to 10% by weight of component (K), based on the weight of the textile, is used.

A further embodiment relates to a method in which a composition is used which comprises 0.01 to 10% by weight of the primer component (P), 70 to 99.9% by weight of the solvent water, and if appropriate 0.01 to 10% by weight of an antimicrobial component (K) and if appropriate from 0.01 to 10% by weight of a metal salt component (M) and also 0.1 to 30% by weight of auxiliary components.

The formulation of the composition can depending on the type of textiles to be treated and depending on the type of methods to be used (e.g. one-bath or two-bath exhaust process in the normal temperature range or in the high temperature range, with or without rinsing or interim drying of the application of the primer component in the exhaust process, followed by the application of the antimicrobial component (K)

with or without the metal salt component (M) in the "one-bath padding process" (thus the classic padding method), spray processes, coating, foam application, "two-bath padding process"; wet in wet or with interim drying).

The invention also relates to a method in which a composition is used which comprises 0.3 to 2.5% by weight of the antimicrobial component (K), 70 to 99.5% by weight of the solvent water and 0.1 to 30% by weight of auxiliary components and if appropriate 0.2 to 2.0% by weight of the metal salt component (M).

A further important subject matter of the invention is a chemical composition for the finishing of textiles or fibers, comprising 0.01 to 20% by weight of a primer component (P), which increases the hydrophobicity of the surface of the textiles or fibers, 70 to 99.5% by weight of the solvent water, and 0.1 to 30% by weight of auxiliary components, and if appropriate 0.01 to 10% by to weight of an organic quaternary ammonium compound as antimicrobial component (K), and if appropriate from 0.01 to 20% by weight, of a metal salt component (M).

A technically useful supply of the metal salt concentration is the antimicrobial active ingredient. The active ingredient is preferably trivalent, i.e. 1 mol of the active ingredient can theoretically completely react with 1 mol of a trivalent metal salt or with 1.5 mol of a divalent salt, and with mixtures correspondingly. The actual use concentrations have been determined experimentally. The salts are often used in excess. For example, per kg of Sanitized T 99-19 (0.91 mol of active ingredient), 1.26 mol of magnesium chloride and 0.31 mol of aluminum chloride can be used. The dilution of these metal salts can be varied and is a question of the ease of handling. The range of the use concentrations of the metal salts can also be based either on the active ingredient or on the textile.

Since these formulations are often subjected to a dilution step prior to use, for example by adding water or through incorporation into a liquor, the individual components may be present in the composition at higher concentrations than upon application on the textile. It is also possible to distribute the components between two or more compositions and to provide them e.g. as a kit (Kit-of-parts).

Preferably, the composition for application of the primer comprises 0.01 to 20% by weight of a primer component (P), 70 to 99.5% by weight of the solvent water and 0.1 to 30% by weight of auxiliary components.

A further embodiment relates to a composition which comprises 0.01 to 20% by weight of a primer component (P), 70 to 95% by weight of the solvent water, 0.1 to 30% by weight of auxiliary components, and likewise 0.01 to 10% by weight of an organic quaternary ammonium compound, and if appropriate from 0.01 to 20% by weight of a metal salt component (M). This composition is particularly suitable e.g. for a "one-bath process".

A further embodiment relates to a composition which comprises 0.01 to 20% by weight of a primer component (P), where the primer component (P) consists of one or more of the following compounds: aromatic mono- and dicarboxylic acids, where these may also be substituted by hydroxy groups; aromatic mono- and diamines, aromatic mono- and dialcohols; aliphatic mono- and dicarboxylic acid having 6 to 26 carbon atoms, where these may also be substituted by hydroxy or amino groups; aliphatic, primary and secondary amines having 6 to 26 carbon atoms; aliphatic, primary and secondary alcohols having 6 to 26 carbon atoms; aliphatic, primary mercaptans having 6 to 26 carbon atoms; amino acids.

The invention also relates to a composition which comprises 0.05 to 15% by weight of a primer component (P), where the primer component (P) consists of one or more of the following compounds: aromatic mono- and dicarboxylic acids, where these may also be substituted by hydroxy groups; aliphatic monocarboxylic acid having 6 to 26 carbon atoms; aliphatic, primary alcohols having 6 to 26 carbon atoms; primary amines having 6 to 26 carbon atoms; natural amino acids.

The invention also relates to a method of producing the compositions described above in which the individual components are mixed. A further aspect of the present invention is the use of a composition described above for the treatment of textiles, fibers and yarns which comprise synthetic materials or consist of synthetic materials for antimicrobial finishing. In this connection, the compositions are particularly suitable for the finishing of textiles made of polyester, polyamide and blends which comprise at least one of these components.

The use preferably takes place for the finishing of textiles, fibers and yarns which consist essentially of polyamide and/or polyester. The finishing of textiles, fibers and yarns takes place e.g. by means of padding processes, foam application, spray processes, coating or exhaust processes (extraction method), it also being possible for two or more of these processes to used in combination. Thus, firstly e.g. the primer can be applied via a padding process or exhaust process and then (if appropriate after drying) an application of the antimicrobial component can take place via a padding process or exhaust process (e.g. jet).

Following the treatment, a (further) drying step d) can preferably take place, e.g. on a tenter or in a tumbler or using a method of contact heating.

When using the "one-bath process", the application of the composition can take place e.g. using a forced application method as in the padding process, by spraying, foam application or by coating. Carrying out an exhaust process is also possible.

The invention further provides textiles, fibers and yarns finished by means of a method as described above. The antimicrobially finished fibers and textiles can be used as a starting material for various materials for a variety of products such as clothing (e.g. women's outer clothing, men's clothing, children's clothing, sport and leisure clothing, protective and occupational clothing, uniforms, linings, socks, stockings and underwear), bedding (e.g. bed cover and sheets), household textiles, seat covers, cushion covers, furniture covers, textiles for shoes, shower curtains, terry toweling articles, cloths, mops, filters, carpets, padding and fleeces, insulating mats, textile wall coverings, curtains, towel rolls, protective articles (e.g. masks and bandages), textiles for automobiles, public transport (trains, buses, airplane, ships, etc.) and the like.

The base fiber used in the present invention may be e.g. a synthetic (chemical) fiber. The chemical fibers are, for example, polyamide fibers, polyester fibers and mixtures thereof. In principle, The method as claimed in the invention can also be used on a polypropylene fiber, polyvinyl fiber, polyacrylic fiber, polyurethane fiber, polyethylene fiber, polyvinylidene fiber and polystyrene fiber. The method can also be used on blends containing synthetic and natural parts.

To achieve the objects specified at the start, numerous experiments have been undertaken to apply or to incorporate molecules as primer component (P) onto the surface or into the near-surface area of the synthetic fibers, which molecules have reactive groups which can then form a covalent bond with the organic quaternary ammonium compound. Suitable binding partners are inter alia those structures which can form a stable bond to the silicon atom of the quaternary ammonium compound of the general formula (I). Of suitability are in particular e.g. compounds which carry at least one acidic hydrogen atom on a heteroatom.

On account of the very high bonding strength of the resulting bond to the silicon atom, groups with the structural element C—OH are preferred. In particular, the organic molecules specified above such as alcohols, phenols, carboxylic acids and amino acids, present themselves here. Also suitable are in addition molecules which carry two or more of the specified groups. In this connection, there is great variability in how the further structure of the molecule looks, compounds carrying amino or mercapto groups are also suitable.

The part of the structure which is not intended to react with the polar group of the quaternary ammonium compound should take on another function. It should be as easy as possible to anchor to the synthetic fiber, e.g. the polyester or polyamide. This is achieved, for example, by the selected molecules in the polyester surface being easy to dissolve.

In this connection, the nonpolar parts of the molecule should be sufficiently large for some of the molecule to be anchored within the polymer and for the functional groups to be available for the formation of the covalent bond e.g. to the siloxane group of the quaternary ammonium compound.

For the finishing with primers (P), in one embodiment of the invention a two-stage process is chosen. Firstly, the primer is applied (process step a). That can be carried out e.g. either in an exhaust process under customary conditions or else in a padding process. The textile is then preferably dried (process step b). In a subsequent process step (c), e.g. by means of padding processes, the quaternary ammonium compound, in particular a compound of the general formula (I), is then applied.

Preferably, a one-bath process is often used, i.e. in a first step, the primer (P) is applied and then in the same bath the antimicrobial component (with and without metal salt component). The liquor is then discharged, if appropriate frequently rinsed and then dried (and if need be also cured).

In the examples below, the following compounds inter alia were tested as primer component (P):
gallic acid (3,4,5-trihydroxybenzoic acid, $m_M$: 170.12 CAS: 149-91-7),
terephthalic acid (benzene-1,4-dicarboxyolic acid, $m_M$: 166.13, CAS: 623-27-8),
tannic acid (gallotannin, tannin, $m_M$:1701.2, CAS: 1401-55-4),
stearic acid (octadecanoic acid, $m_M$: 284.48, CAS: 57-11-4),
octadecylamine (mM:269.51, CAS: 124-30-1),
various amino acids, e.g. L-phenylalanine (mM:165.19, CAS: 63-91-2).

Figure 1:
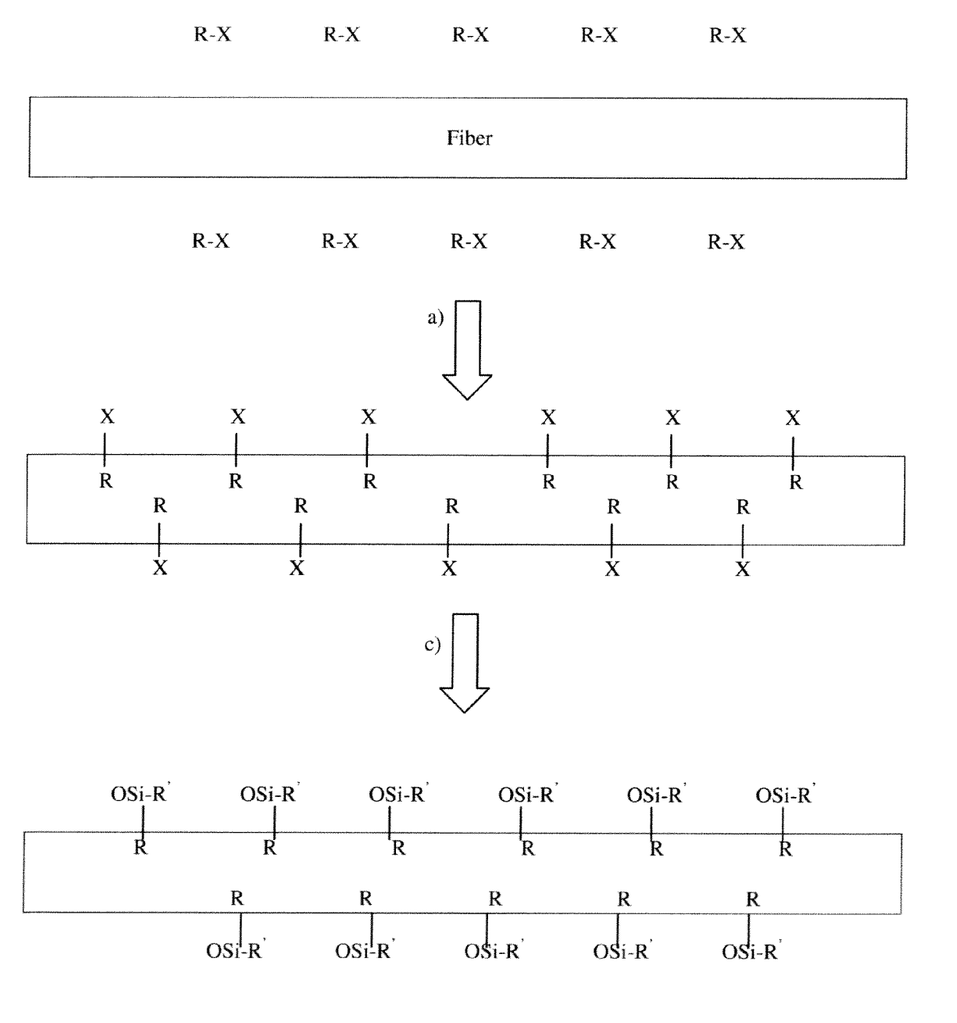

A model explanation of the process used for the antimicrobial finishing is shown diagrammatically in FIG. 1, these data in no way to be interpreted as limiting. A primer component (P), e.g. a compound R—X, where R is e.g. an alkyl radical and X is e.g. a carboxyl group, is applied to a fiber.

In process step a), the fiber is treated with the aqueous solution of the primer and if appropriate heat, addition of acid or base, surfactants, carrier agents and/or reducing agents.

This produces the fiber finished with the primer. This can then be dried, if appropriate.

In process step c), the quaternary ammonium compound is then applied, e.g. an organosilicon amine with an alkyl group R' as described above. This produces the fibers with a long-lasting finish.

The invention thus also relates to an in situ prepared composition which, besides the solvent water, comprises on the one hand 0.05 to 15% by weight of a primer component (P), in particular of the following primer components (P): aromatic mono- or dicarboxylic acids, where these may also be substituted by hydroxy groups; aliphatic monocarboxylic acid having 6 to 26 carbon atoms; aliphatic, primary alcohols having 6 to 26 carbon atoms; primary amines having 6 to 26 carbon atoms; natural amino acids; and that on the other hand it comprises 0.01 to 10% by weight of antimicrobial components, in particular of dimethyl-tetradecyl-(3-(trimethoxysilyl)-propyl)-ammonium salt or dimethyl-octadecyl-(3-(trimethoxysilyl)-propyl)-ammonium salt, and additionally if appropriate comprises a metal salt component (M) which consists of at least one salt of a divalent metal from the group Mg, Ca, Zn, Ba and/or a salt of a trivalent metal from the group Al and Fe.

The examples below illustrate further important aspects of the invention.

EXAMPLE 1

Two-Bath Process

Process Step a)

1.88 g of L-phenylalanine (as primer component (P)) are dissolved in 950 g of water. Using acetic acid, the pH is adjusted to 4.5 and the mixture is topped up to 1000 g with water. 125 g of fabric made of polyester with a weight per area of ca. 220 g/m$^2$ are divided between four pots and in each case an eight-fold amount of the fabric weight of the prepared liquor is added. The pots are sealed and the exhaust process is carried out using a customary device (Mathis Labomat BFA-12). During this, the pots are heated to 120° C. at a heating rate of 3° C./min. The temperature of 120° C. is maintained for 45 minutes and is then cooled to 40° C. at 3° C./min.

Process Step b)

The samples are then briefly rinsed in cold water, spun and dried in each case for 2 minutes on the tenter at 120° C. The theoretical amount of L-phenylalanine on the textile is 1.5%, based on the dry fabric weight.

Process Step c)

980 g of water are added to a beaker. 1 g of a nonionogenic silicone- and solvent-free wetting agent, detergent and cleaner (Hostapal MRN from the manufacturer Clariant, Switzerland; based on a polyglycol ether derivative) and 1 g of acetic acid (80% strength) are added with stirring. As antimicrobial compound of the general formula (I), 18 g of Sanitized T 99-19 (as described above) are then added and the bath is stirred until it is homogeneous.

Padding is used to apply this liquor to the polyester samples which have been coated beforehand with L-phenylalanine. The pick-up is 36% and consequently the absorption of Sanitized T 99-19 is just 0.64%, based on the dry fabric weight.

Further Drying Step

The samples are dried on the tenter at 120° C. for 2 minutes.

Testing of the Finished Textiles

The samples are then washed at 40° C. in accordance with EN ISO 6330 (6A) and in each case tested for *Staphylococcus aureus* ATCC 6538 in accordance with ASTM E 2149 after 10, 20 and 30 wash cycles.

The germ reduction is still above $10^2$ even after 30 wash cycles compared to the unfinished sample and is thus excellent.

EXAMPLE 2

Procedure analogous to example 1, but with 3.1 g of L-phenylalanine in the exhaust liquor. This corresponds to 2.5% of the amino acid based on the dry fabric weight. The germ reduction is as in the case for example 1 within the limits of the variance of the method and thus excellent.

EXAMPLES 3 and 4

Analogously to examples 1 and 2, L-phenylalanine is firstly applied in the exhaust process to polyester fabric (Dacron 54 spun) with a weight per area of ca. 120 g/m$^2$.

On account of the lower weight per area of the textile, significantly more, namely 0.9%, of Sanitized T 99-19 is applied, meaning that a similar mass of the product per unit area is available. In these experiments also, a germ reduction of somewhat above 10$^2$ is achieved after 30 wash cycles.

EXAMPLES 5 to 8

In these examples, in each case another polyester type is finished in each case with 1.5 or 2.5% L-phenylalanine. In examples 5 and 6, where a polyester type (Interlock with ca. 200 g/used, finishing is carried out with 0.6% Sanitized T 99-19 and in examples 7 and 8 with a polyester fabric (from Tersuisse) with 230 g/m$^2$ likewise with 0.6 g/m$^2$. These samples also exhibit a reduction in the germ count after 30 wash cycles of at least 2 decimal powers compared to the starting value.

Through these examples, it shown that the type and origin of the polyester exhibits no significant influence on the antibacterial result even after repeated washing.

Since the use of amino acids as textile chemical is not a customary method in the textile industry and, moreover, the finishing can significantly increase the cost of the product, further systems are also tested.

EXAMPLES 9 and 10

1.25 g or 2.5 g, respectively, of stearic acid are dispersed in 990 g of water at room temperature and admixed with 1.5 or 3 g, respectively, of potassium hydroxide. Stir for 90 minutes on the magnetic stirrer at room temperature and then adjust to pH 6.5 with acetic acid. These liquors are then applied analogously to example 1 to polyester Trevira with a weight per area of ca. 220 g/m$^2$ and dried.

In example 9 with 1.0% stearic acid on the fabric, 0.6% Sanitized T 99-19 is applied to the polyester and in example 10 with 2.0% stearic acid on the fabric, 0.8% Sanitized T 99-19 is applied using padding processes.

After 20 wash cycles, in the case of example 9, a reduction in the germ count by just below 3 decimal powers is found and in the case of example 9 even by a good four decimal powers.

The use of a long-chain carboxylic acid to achieve the object works generally, i.e. it is possible to apply the Sanitized T 99-19 also to polyester which is finished with e.g. stearic acid as primer (P), in a wash-resistant manner according to the objective.

EXAMPLES 11 to 13

Instead of stearic acid, 2.5 g of tannic acid are dissolved in water and adjusted to 1000 g. The advantage of this acid is the good solubility in water. The application to the polyester fabric was carried out exactly as described in example 1 except that in the case of this and the two following examples, in each case 12 g of acetic acid were added per liter.

However, the textile becomes severely discolored during the treatment. It is finished as described in example 1 by means of the padding method with 0.6% Sanitized T 99-19 and tested. After 20 wash cycles, a reduction in the germ count by a factor greater than ten compared with the control sample is still found. However, the severe discoloration of the liquor and of the textile is not very desirable.

Besides 1.5 g of tannic acid, the same amount of sodium disulfite (Na$_2$S$_2$O$_5$) is then dissolved in water, topped up to 1000 g and again applied to polyester using the exhaust process according to example 1. As a result, the discoloration of the liquor and textile can be largely suppressed.

The antibacterial values following application of Sanitized T 99-19 with subsequent washing also exhibits better values than in the example previously, but per se still only adequate.

Particularly good results are achieved by, besides 1.5 g of tannic acid, dissolving 1.5 g of sodium sulfite (Na$_2$SO$_3$) in water and topping up to 1000 g. The antibacterial values following application of Sanitized T 99-19 with subsequent washing also exhibit improved values. With sodium thiosulfate it is not possible to prevent the discoloration.

EXAMPLES 14 to 16

Examples 14 to 16 are carried out analogously to examples 11 to 13.

Instead of the tannic acid, 1.5 g of gallic acid monohydrate are used per liter of liquor, and in examples 15 and 16 with in each case 1.5 g of sodium disulfite or sodium sulfite. However, the gallic acid does not exhibit these severe discolorations like tannic acid.

After 20 wash cycles, the reduction in the germ count is increasing from examples 14 to 16 from a reduction of somewhat above one decimal power to almost two decimal powers to somewhat above two decimal powers.

EXAMPLES 17 and 18

It is attempted to further increase the resistance to washing by reductively cleaning the polyester fabric prior to the application of the gallic acid or tannic acid.

For this, the textile is treated at 80° C. with a 10-fold mass of a solution of 5 g/l of sodium dithionite, 8 g/l of a 20% strength sodium hydroxide solution and 5 g/l of Hostapal MRN (manufacturer: Clariant) for 20 minutes.

The solution is then removed and the textile is rinsed with ca. 50° C. hot water and then with ca. 15° C. cold water, spun and dried. The textile pretreated in this way is treated with an aqueous solution of 0.15% of tannic acid or 0.15% of gallic acid monohydrate, respectively, at 40° C. for 20 minutes and a liquor ratio of 1:10. The solution is poured off, the textile is briefly rinsed cold, spun and dried on the tenter at 120° C. for 2 minutes.

The textile pretreated as described and coated with primers (P) is finished in the padding process with 0.5% Sanitized T 99-19 and then dried for two minutes on the tenter at 120° C.

These samples are washed in steps up to 30 wash cycles and tested for *Staphylococcus aureus* ATCC 6538 in accordance with JISL 1902:2002. The results of the samples with the tannic acid as primer are poorer and, after 20 wash cycles, still achieve a germ count reduction of 10$^{15}$ compared with the samples with gallic acid as primer, where the reduction in the germ count after 30 cycles is still 10$^{2.0}$.

In further experiments, it is ascertained that the exhaust conditions of gallic acid at temperatures at 80° C. produce better results than if the exhaust is carried out under high-temperature conditions, in the experiments 120° C. It is likewise ascertained that the use amount has no significant influence in a very broad range from 1% to 2.5% gallic acid, based on the mass of the textile.

The use of terephthalic acid and octadecylamine as primer (P) exhibits an improvement in the antimicrobial effect after washing, although the effect is less pronounced than in the case of the substances tannic acid, gallic acid or stearic acid or in particular L-phenylalanine.

EXAMPLE 19

1.88 g of L-phenylalanine are dissolved in 950 g of water, the pH is adjusted to 4.5 with acetic acid and the mixture is topped up to 1000 g with water. 125 g of fabric made of polyester having a weight per area of ca. 220 g/m² are divided between four pots and in each case an eight-fold amount of the fabric weight of the prepared liquor is added. The pots are sealed and the exhaust process is carried out using a Mathis Labomat BFA-12. Here, the pots are heated to 80° C. at a heating rate of 3° C./min.

80° C. is maintained for 60 minutes and then the mixtures are cooled to 40° C. at 3° C./min. The samples are briefly rinsed in cold water, spun and dried at 120° C. on the tenter for 2 minutes in each case. The theoretical amount of L-phenylalanine on the textile is 1.5%, based on the dry fabric weight.

782 g of water are placed in a beaker. 1 g of Hostapal MRN (a nonionogenic silicone- and solvent-free wetting agent, detergent and cleaner from Clariant based on a polyglycol ether derivative) and 1 g of acetic acid 80% are added with stirring.

216 g of dimethyloctadecyl[3-(trimethoxysilyl)propyl] ammonium chloride as aqueous solution (available under the trade name Aegis AEM 5772/5) are added and the bath is stirred until it is homogeneous. Padding is used to apply this liquor to the polyester samples which have been coated with L-phenylalanine.

The pick-up is 38% and thus the absorption of the aqueous solution of the dimethyloctadecyl[3-(trimethoxysilyl)propyl] ammonium chloride is 8.2%, based on the dry fabric weight. The samples are dried on the tenter at 120° C. for 2 minutes. The samples are washed at 40° C. in accordance with EN ISO 6330 (6A) and tested in each case after 10 and 20 wash cycles for *Staphylococcus aureus* ATCC 6538 in accordance with JIS L 1902:2002.

Even after 20 wash cycles, the germ count found is barely 1% compared with the unfinished sample and the antibacterial effect of the finished sample is therefore good.

EXAMPLE 20

Two effects for increasing the resistance to washing of the Sanitized T 99-19 on polyester fabric are coupled.

Firstly, a primer (P) is applied to the textile, this is carried out as described in example 1; the Sanitized T 99-19 is then reacted in aqueous solution firstly with metal ions, in particular those of 2- to 4-valent metals. Of particular effectiveness here is the mixture of calcium and aluminum ions, with the aim of lowering the solubility of the resulting product as soon as it is applied to the textile.

The textile finished in this way is dried on the tenter and cured.

2.5 g of L-phenylalanine are dissolved in 950 g of water, the pH is adjusted to 4.5 with acetic acid and the mixture is topped up to 1000 g with water. 125 g of polyester fabric with a weight per area of ca. 220 g/m² are divided between four pots and in each case the eight-fold amount of the fabric weight of the prepared liquor is added. The pots are sealed and the exhaust process is carried out using a Mathis Labomat BFA-12. Here, the pots are heated to 80° C. at a heating rate of 3° C./min. 80° C. is maintained for 60 minutes and then the mixture is cooled to 40° C. at 3° C./min.

The samples are briefly rinsed in cold water, spun and dried at 120° C. on the tenter for 2 minutes in each case. The theoretical amount of L-phenylalanine in the textile is thus 2%, based on the dry fabric weight.

400 ml of water are initially introduced in a beaker; on a magnetic stirrer, the following are added in succession: 0.3 g of aluminum chloride hexahydrate, 0.99 g of sodium acetate trihydrate, 0.38 g of calcium hydroxide, 2.47 g of acetic acid 80%, 25 g of isopropanol and 4.05 g of Sanitized T 99-19. The solution is topped up to 500 g with water and afterstirred at room temperature for 30 minutes.

Formic acid is used to adjust the pH to 3 and this liquor is applied to the polyester fabric which has been treated with L-phenylalanine in a padding process, during which, at a pick-up of 75%, a concentration of 0.6% of Sanitized T 99-19 ends up on the textile.

The textile is then dried on the tenter for 1 minute at 120° C. and then cured for two minutes at 150° C. After 30 wash cycles in accordance with EN ISO 6330 (6A) at 40° C., in the test according to JIS L 1902:2002, a reduction in the germ count of $10^{2.8}$ is measured, which is an excellent value.

In order to make the application as easy as possible for the textile industry, the system is designed such that it can be applied in the "one-bath process".

In this connection, it is established that it is barely possible to prepare the quaternary ammonium compound of the formula (I) together with the products which are to be used as primers (P) in aqueous solution in a storage-stable manner in concentrations which are of interest for marketing the product as a finished, ready-to-use mixture. The mixture changes considerably within a very short period. Consequently, another route was pursued so that the user should preferably handle two formulations.

EXAMPLE 21

Finishing in the "One-Bath Process"

20 g of L-phenylalanine are dissolved in 973.1 g of water and admixed with 2.0 g of sodium acetate trhydrate and 4.9 g of acetic acid.

885 g of water are initially introduced and to this are added 100 g of the phenylalanine solution with the acetate buffer which primarily has the purpose of preventing yellowing on delicate textiles. 15 g of Sanitized T99-19 are stirred in. This mixture is applied by means of padding both to fabric made of polyester and also to fabric made of polyamide, such that between 0.6 and 0.8% of Sanitized T99-19 end up on the fabric. The fabrics finished in this way are dried at 120° C. on the tenter for two minutes and then cured for 45 seconds at 150° C.

The fabrics are washed 20 times at 40° C. and then tested for *Staphylococcus aureus* ATCC 6538 P in accordance with ASTM E 21-49. All of the samples show a germ reduction of more than two decimal powers.

EXAMPLE 22 a) 188 g of water are initially introduced, 2 g of gallic acid are added and 10 g of Sanitized T 99-19 are added with stirring. Stir for 45 minutes at room temperature, top up to 750 g with water and stir in for 15 minutes at room temperature and then apply in a padding process to polyester fabric with a pick-up of 38%, such that the absorption of Sanitized T 99-19 is 0.5%. b) The same liquor is applied to polyamide fabric, where in the case of a pick-up of 60%, an absorption of 0.8% of Sanitized T 99-19, based on the textile mass, is achieved.

The two samples finished in this way are washed at 40° C. and dried between the washing cycles. After 20 and 30 washing cycles, the antibacterial effect against *Staphylococcus aureus* 6538 P is tested. In all of the tests, both textile types exhibit a good antibacterial effect, although the effect becomes significantly weaker than in the unwashed state, though a germ reduction rate of more than 99.99% is also achieved here.

EXAMPLE 23

Finishing in the "One-Bath Process" with Metal Component

In order to obtain even better resistance to washing, it is attempted to crosslink the trimethoxysilicon group of the quaternary ammonium compound via at least divalent metal ions and at the same time the intention was to incorporate a primer.

910 g of water are initially introduced and into this are dissolved in succession, with stirring using a magnetic stirrer: 10 g of L-phenylalanine, 0 g of aluminum chloride hexahydrate, 11.2 g of calcium chloride, 1.6 g of sodium acetate trihydrate and 3.9 g of 80% strength acetic acid.

150 g of this solution are added to 835 g of water and to this are added 15 g of Sanitized T 99-19. This mixture is stirred for 45 minutes at room temperature and then applied to polyester fabric by means of padding.

The pick-up is 41% and thus the absorption of Sanitized T 99-19 is 0.6%, based on the dry textile weight.

The fabric samples are dried and cured at 150° C. on the tenter for 2 minutes and then washed in steps up to 30 wash cycles at 40° C. in accordance with EN ISO 6330 (6A) using ECE 77 colorfast detergent and tested for *Staphylococcus aureus* 6538 in accordance with ASTM E 21-49. All of the samples exhibit a good antibacterial effect.

EXAMPLE 24

94 g of water are initially introduced, 1 g of gallic acid is added and 5 g of Sanitized T 99-19 are added with stirring. Stir at room temperature for 45 minutes.

Per tube, 50 g of polyester fabric are weighed in and to this is added a solution of 5 g of the described solution in 400 g of water. The tubes are screwed shut and with permanent rotatory motion heated to 120° C. by 3° C. per minute, and then held at 120° C. for 30 minutes, and cooled to 40° C. at 3° C. per minute.

The liquor is poured off and the textile sample is briefly rinsed with cold water, spun and then dried on the tenter at 130° C. for 3 minutes.

The samples are washed in steps at 40° C. up to 30 wash cycles and tested for *Staphylococcus aureus* 6538 in accordance with ASTM E 21-49. The samples exhibit a good antibacterial effect up to 15 wash cycles.

EXAMPLE 25

2 g of phenylalanine are dissolved in 92 g of water, 1 g of acetic acid 80% is added. With stirring, 5 g of Sanitized T 99-19 are added. Afterstir for 1 hour at room temperature. In each case 50 g of fabric made of polyamide or of polyester are treated with a mixture of 400 g of water and 5 g of the solution containing phenylalanine/Sanitized T 99-19 in an exhaust tube. Screwed shut and with permanent rotatory motion, the tubes are heated by 3° C. per minute to 120° C. in the case of the polyester, or to 80° C. in the case of the polyamide and then held for 30 minutes at 120° C. or at 80° C., respectively, cooled to 40° C. at 3° C. per minute.

The liquor is poured off and the textile sample is briefly rinsed with cold water, spun and then dried on the tenter at 130° C. for 3 minutes.

The samples are washed at 40° C. up to 30 wash cycles and tested for *Staphylococcus aureus* 6538 in steps of five in accordance with ASTM E 21-49. The samples exhibit a very good antibacterial effect up to 10 wash cycles in the case of polyamide, and 15 wash cycles in the case of polyester.

EXAMPLE 26

964 g of water are initially introduced into a beaker. To this are added, with stirring, in succession 2.2 g of L-phenylalanine, 2.0 g of sodium acetate trihydrate, 4.9 g of 80% strength acetic acid, 2.5 g of zinc chloride, 1.4 g of aluminum chloride hexahydrate, the mixture is stirred for 5 minutes at room temperature and then 20 g of Sanitized T 99-19 are added.

This mixture is stirred for one hour at room temperature. 100 ml of the mixture are stirred into 2550 g of water. The pH is adjusted to 4.0 and in this weakly acetic acid solution, a polyester fabric weighing 330 g (Trevira with a weight per area of ca. 220 g/m$^2$) is exhausted in a high-temperature process, the mixture being heated to 120° C. at a rate of 3° C. per minute, held at 120° C. for 30 minutes and then cooled again to 40° C. at 3° C. per minute. The liquor is separated off and the textile is briefly rinsed in cold water and then dried on the tenter for 3 minutes at 130° C.

The textile is washed at 40° C., with drying after 1, 3, 5, 10, 15, 20, 25 and 30 wash cycles. The samples are washed at 40° C. up to 30 wash cycles and tested for *Staphylococcus aureus* 6538 in steps of five in accordance with ASTM E 21-49. The samples exhibit a very good antibacterial effect up to 20 wash cycles, and in the case of 25 wash cycles still exhibit an antibacterial effect which is adequate in practice.

EXAMPLE 27

2560 g of water are initially introduced into a beaker. To this are added with stirring, in succession, 0.36 g of L-phenylalanine, 0.20 g of sodium acetate trihydrate, 0.49 g of 80% strength acetic acid, 0.18 g of calcium chloride, 0.09 g of aluminum chloride hexahydrate.

The mixture is stirred for 5 minutes at room temperature and then 2.0 g of Sanitized T 99-19 are added. This mixture is stirred for one hour at room temperature. The pH is adjusted to 4.0 and in this weakly acetic acid solution, a polyester fabric weighing 330 g (Trevira with a weight per area of ca. 220 g/m$^2$) is exhausted in a high-temperature process, during which the mixture is heated to 120° C. at a rate of 3° C. per minute, held at 120° C. for 30 minutes and then cooled to 40° C. again at 3° C. per minute.

The liquor is then separated off and the textile is briefly rinsed in cold water and then dried on the tenter for 3 minutes at 130° C. The textile is washed at 40° C., drying after 1, 3, 5, 10, 15, 20, 25 and 30 wash cycles.

The samples are washed at 40° C. up to 30 wash cycles and tested for *Staphylococcus aureus* 6538P in steps of five in accordance with ASTM E 21-49. The samples exhibit a very good antibacterial effect to 20 wash cycles and an adequate antibacterial effect in the case of 25 wash cycles, with a reduction in the germ count of about a factor of 100 compared to an unfinished sample.

EXAMPLE 28

An antimony-free, anthracite-colored, reductively cleaned and rinsed fabric made of pure polyester measuring 200 linear meters in length and 1.6 meters in width and having a weight per area of 175 grams per square meter, thus in total 56 kilograms of textile, are inserted into a jet (machine for technical exhaust processes).

500 liters of water are added and a solution of 1.08 kilograms of L-phenylalanine in 50 liters of water and 165 grams of formic acid are added, the pH of the liquor is 5. Allow to prerun for five minutes, then heat to 60° C. at a heating rate of 2° C. per minute. Leave for 20 minutes at 60° C.

325 grams of Sanitized T99-19 in 10 liters of water are added and the jet is left running for a further 20 minutes at 60° C. 1.7 kilograms of bethamine AHP (wax/fatty acid condensation product from Dr. Th. Böhme KG Chemische Fabrik GmbH & Co., Isardamm 79-83, D-82538 Geretsried, a universal soft handle agent, hydrophilic with exceptional antistatic properties) are added, left to run for a further 15 minutes at 60° C. Cooled at 2° C. per minute and the liquor is drawn off, rinsed with 150 liters of water, the rinse water is drawn off and the textile is dried on the tenter at 120° C. for 2 minutes.

Samples of this textile are washed in accordance with the standard EN ISO 6330 (6A) at 40° C. using the colorfast detergent in accordance with the standard ECE 77. After 30, 40 and 50 wash cycles, the germ reduction is tested for *Staphylococcus aureus* ATCC 6538 using the method in accordance with ASTM E 21-96. The results are a germ reduction at all test points of 1.6 to 1.7 units according to the base-ten logarithm, corresponding to a survival rate of from 2 to 3 percent of the test germs.

EXAMPLE 29

In an experimental finishing. 14 kilograms of an orange colored tricot made of polyester/polyamide/elastan are prewashed at 60° C., then 280 grams of L-phenylalanine and 110 liters of water are added. Allow to prerun for 10 minutes, heated to 60° C. at 3° C. per minute and left to run for 15 minutes at 60° C. 80 grams of Sanitized T 99-19 in 2 liters of water are added and left to run for a further 30 minutes at 60° C. The liquor is cooled to 35° C. and then drawn off. 40 liters of water for rinsing are added, left to run for two minutes and the rinse water is drawn off. The textile is discharged via press-off rolls and dried on a tenter at 120° C. After 50 washing cycles in accordance with EN ISO 6330 (6A), washed with the colorfast detergent according to ECE 77, a sample achieves a germ count reduction of factor 100 (log reduction=2.0) compared with the inoculum.

The invention claimed is:

1. A method for the antimicrobial finishing of textiles, fibers, or yarns which consist essentially of synthetic materials, comprising the step of applying to a textile, fiber, or yarn:
   an aqueous solution comprising 0.01 to 3% by weight of an organic primer component (P), which increases the hydrophobicity of the surface of the textiles or fibers, wherein the primer component (P) is phenylalanine;
   70 to 99.5% by weight of the solvent water;
   0.1 to 30% by weight of auxiliary components;
   0.01 to 3% by weight of an organic quaternary ammonium compound of the general formula (I) as an antimicrobial component (K)

(I)

wherein the radicals, independently of one another, have the following meanings,
$R^1$, $R^2$, and $R^3$ are identical and are a branched or unbranched alkyl radical having 1 to 4 carbon atoms;
$R^4$ is methyl;
$R^5$ is a branched or unbranched alkyl radical having 1 to 18 carbon atoms;
$R^6$ is a branched or unbranched alkyl radical having 8 to 18 carbon atoms; and
n is an integer from 1 to 4; and
0.01 to 2% by weight of a metal salt component (M) comprising at least one salt of a divalent metal selected from the group consisting of Mg, Ca, Ba, Zn and/or a salt of a trivalent metal from the group Al and Fe.

2. The method as claimed in claim 1, wherein the antimicrobial component (K) comprises a dimethyltetradecyl(3(trimethoxysilyl)propyl)ammonium salt or a dimethyloctadecyl (3-(trimethoxysilyl)propyl)ammonium salt, and wherein the metal salt component (M) comprises a salt of a divalent metal from the group Mg, Ca, Zn, Ba and/or a salt of a trivalent metal from the group Al and Fe.

3. The method as claimed in claim 1 wherein the textile, fiber or yarn consist essentially of a polyamide, a polyester, or combinations thereof.

4. The method as claimed in claim 1 wherein the application step comprises a padding process, foam application, a spray process, a coating method or an extraction method.

5. A composition for the finishing of textiles or fibers, comprising
   0.01 to 3% by weight of a primer component (P), which increases the hydrophobicity of the surface of the textiles or fibers, wherein the primer component (P) is phenylalanine;
   70 to 99.5% by weight of the solvent water,
   0.1 to 30% by weight of auxiliary components,
   0.01 to 3% by weight of an organic quaternary ammonium compound of the general formula (I) as antimicrobial component (K)

(I)

wherein the radicals, independently of one another, have the following meanings,
$R^1$, $R^2$, and $R^3$ are identical and are a branched or unbranched alkyl radical having 1 to 4 carbon atoms;
$R^4$ is methyl;
$R^5$ is a branched or unbranched alkyl radical having 1 to 18 carbon atoms;
$R^6$ is a branched or unbranched alkyl radical having 8 to 18 carbon atoms; and
n is an integer from 1 to 4, and
from 0.01 to 2% by weight of a metal salt component (M) comprising at least one salt of a divalent metal selected from the group consisting of Mg, Ca, Ba, Zn and/or a salt of a trivalent metal from the group Al and Fe.

6. The composition as claimed in claim 5, characterized in that, besides the solvent water, it comprises:
   0.05 to 3% by weight of the primer component (P); and
   0.01 to 3% by weight of dimethyltetradecyl(3-(trimethoxysilyl)propyl)ammonium salt or dimethyloctadecyl(3-(trimethoxysilyl)propyl)ammonium salt.

* * * * *